United States Patent [19]

Everest

[11] Patent Number: 5,046,482
[45] Date of Patent: Sep. 10, 1991

[54] DISPOSABLE INFRARED THERMOMETER INSERTION PROBE

[75] Inventor: Charles E. Everest, Santa Ana, Calif.

[73] Assignee: IVAC Corporation, San Diego, Calif.

[21] Appl. No.: 428,416

[22] Filed: Oct. 27, 1989

Related U.S. Application Data

[63] Continuation of Ser. No. 176,169, Mar. 31, 1988, abandoned.

[51] Int. Cl.$^5$ .......................... A61B 1/22; G01K 1/08
[52] U.S. Cl. ........................................ 128/9; 128/664; 374/130; 374/158
[58] Field of Search .................. 128/736, 9, 664, 666, 128/4, 5; D10/57; 250/338; 374/126, 129, 158, 209, 120, 121, 130, 131

[56] References Cited

U.S. PATENT DOCUMENTS

| | | | |
|---|---|---|---|
| 3,282,106 | 11/1966 | Barnes | 73/355 |
| 3,531,992 | 10/1970 | Moore | 73/359 |
| 3,581,570 | 6/1971 | Wertz | 128/736 |
| 3,751,664 | 8/1973 | Falbel | 374/130 |
| 3,878,836 | 4/1975 | Twentier | 128/9 |
| 4,602,642 | 7/1986 | O'Hara et al. | 128/664 |
| 4,634,294 | 1/1987 | Christol et al. | 374/130 |
| 4,662,360 | 5/1987 | O'Hara et al. | 128/9 |

OTHER PUBLICATIONS

Wolfe, William L., Zissis, George J., eds., The Infrared Handbook pp. 9-12 to 9-14, 1978.
Smith, Warren, Modern Optical Engineering, pp. 234-236.

Primary Examiner—Edward M. Coven
Assistant Examiner—Mark J. Graham
Attorney, Agent, or Firm—Fulwider, Patton, Lee & Utecht

[57] ABSTRACT

A disposable cone channel insertion probe is adapted for use in combination with an infrared thermometer. The probe has a generally frusto-conical hollow body portion, an inner reflective surface, and a flange projecting radially outward from the rearward end of the probe. The infrared thermometer also includes a mechanism for retaining the probe and optics for further focusing and collimating the infrared light from the probe to an infrared sensor.

4 Claims, 2 Drawing Sheets

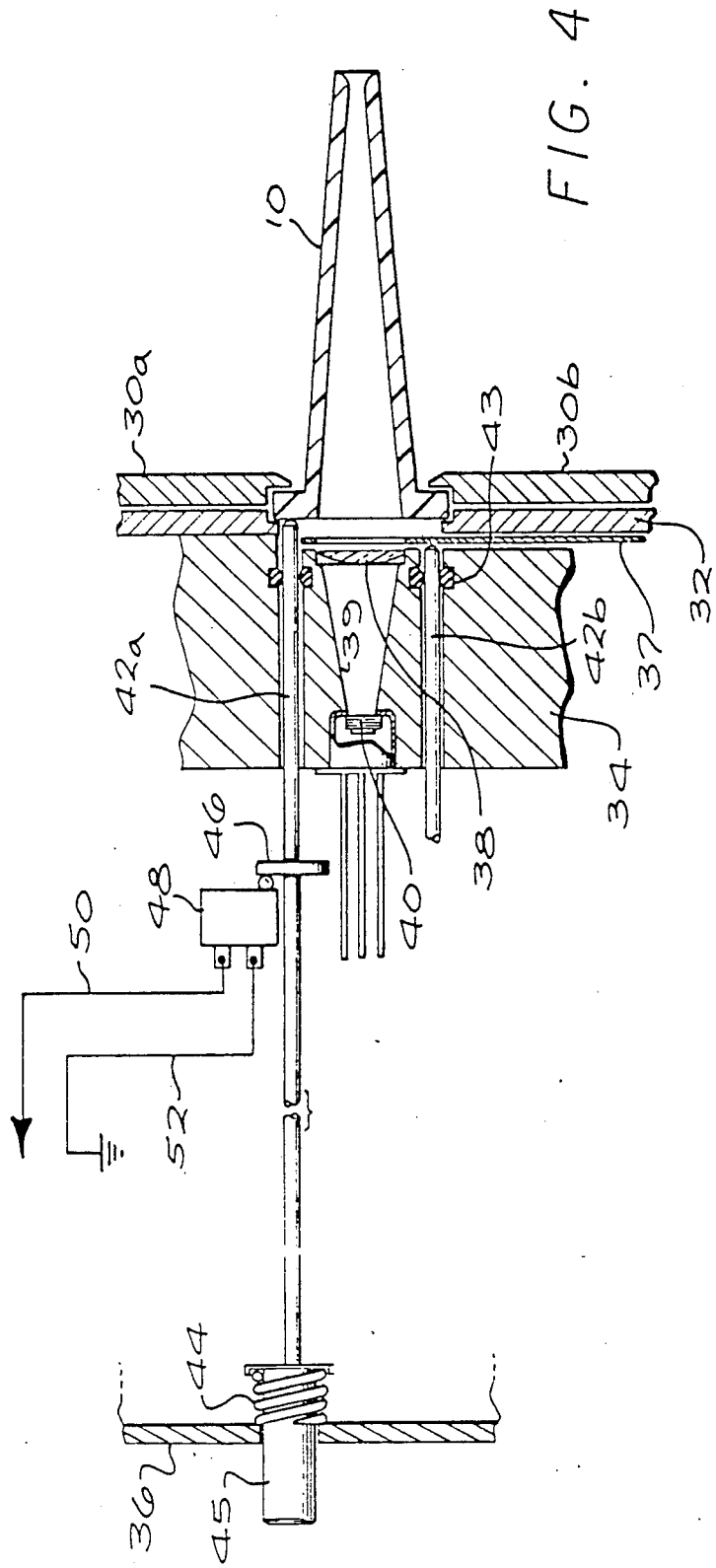
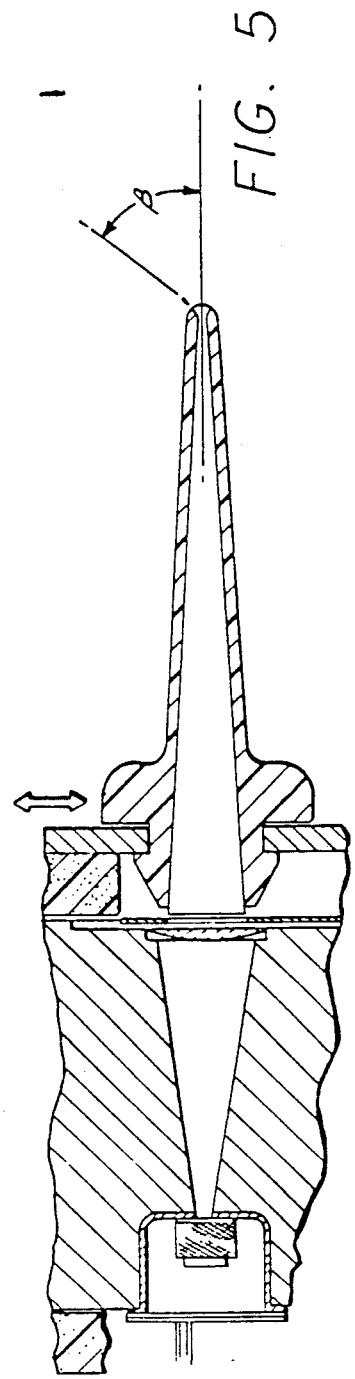

DISPOSABLE INFRARED THERMOMETER INSERTION PROBE

This application is a continuation, of application Ser. No. 07/176,169, filed Mar. 31, 1989.

BACKGROUND OF THE INVENTION

1. Field of the Invention

This invention relates generally to infrared thermometers, and more particularly to a disposable insertion probe for use with a medical infrared thermometer.

2. Prior Art

Medical thermometers are useful in the diagnosis and treatment of many diseases. Measurement of a patient's body temperature has been most commonly performed by conventional mercury thermometers. Disadvantages of such thermometers are that accurate readings often require a minute or more, and such thermometers need to be sterilized before each use. Electronic thermometers have become popular because they require far less time for an accurate reading of a patients temperature, and the probe of the electronic thermometer is commonly inserted into a protective disposable cover before use. Such electronic thermometers are rapidly reusable and are generally sanitary when used with sanitary sheaths. However, an accurate reading of a patient's temperature still may require as much as 30 seconds, since the temperature is measured through the sanitary sheath which must equilibrate to the patient's temperature. Such thermometers are also generally used orally or rectally.

The auditory canal and the tympanic membrane are also useful for measurement of a patient's internal body temperature. An electronic thermometer utilizing a thermocouple for measuring the temperature of the tympanic membrane by directly contacting the tympanic membrane is described, for example, in U.S. Pat. No. 3,531,992. However, such devices have the disadvantage of causing discomfort to the patient, and the probe is either inserted without a sheath, thus requiring sterilization between uses, or else utilization of a sheath or speculum generally prolongs the time in which temperature is measured.

Infrared thermometers avoid the necessity of contacting the location at which temperature is actually being measured, and have also been designed for use in measuring the patient's temperature from the auditory canal or from the tympanic membrane. One such device is described in U.S. Pat. No. 3,282,106 (Barnes). An infrared detector receives infrared radiation from the auditory canal through an internally polished truncated cone which serves as a shield and an insulator, so that temperature readings are only taken from the auditory canal. A similar infrared thermometer for measuring body temperature through the auditory canal is described in U.S. Pat. No. 3,878,836, (Twentier) which focuses the insertion probe of the device toward the tympanic membrane. A disposable speculum is also placed completely over the insertion probe for sanitary purposes. However, the speculum and probe are open at the forward end, allowing contamination of the probe by earwax or other debris, so that the insertion probe actually requires cleaning sterilization to be assured of sterile and effective use. A disposable speculum for an infrared thermometer insertion probe is also described in U.S. Pat. No. 4,662,360 (O'Hara et al.), but this disposable speculum also includes a film of protective plastic material at the forward end of the speculum to prevent contamination and clogging of the insertion probe. The film covering the disposable speculum is substantially transparent to infrared radiation. The body portion of the speculum fits onto the insertion probe so that the membrane is stretched tightly over the tip of the insertion probe, to remove any wrinkles in the membrane. An infrared thermometer with which the disposable speculum may be used is also shown in U.S. Pat. No. 4,602,642 (O'Hara et al.) There remains the disadvantage with this type of thermometer that a certain amount of infrared radiation is still absorbed by the film over the speculum, and the pressure of the insertion probe against the membrane allows for the possibility of breakage of the protective membrane during a temperature measurement due to stresses placed on the speculum and insertion probe, and possibly due to manufacturing defects in the membrane itself, or in the attachment of the membrane to the speculum. Other problems in achieving an accurate temperature reading can be caused by the film membrane, so that it would be desirable to have the forward end of the insertion probe not covered by a protective membrane. It is at the same time desirable to avoid contamination of the insertion probe, which may lead to the spread of infection from patient to patient or which would otherwise require cleaning and sterilization between uses. An infrared thermometer with such an insertion probe could be rapidly reused, and could provide accurate readings, in a matter of a few seconds, or less.

SUMMARY OF THE INVENTION

The present invention provides a probe for use with an infrared radiation detecting device having means for retaining the probe and means for focusing infrared radiation transmitted through the probe to an infrared sensor. The probe has a generally frusto-conical hollow body portion with open ends, and an inner reflective surface. A flange projecting radially outward from the body portion is adapted to abut a portion of the infrared detecting device. The probe is easily removed from the infrared radiation detecting device, which may be used as a medical infrared thermometer. The insertion probe serves as a negative cone channel objective lens, to collimate infrared radiation from a wide acceptance angle, so that the probe may be used for taking temperature readings from inside surfaces of cavities and animal or human bodies.

Briefly and in general terms, a probe according to the invention, for use in combination with an infrared detecting device having means for retaining the probe and means for focusing infrared radiation transmitted through the probe to an infrared sensor, comprises a generally frusto-conical hollow body portion having a narrow forward end and a wide rearward end, the body portion being open at each end; with the body portion having an inner reflective surface, and a flange projecting radially outward from the body portion for abutting a portion of the device. The body portion is also preferably made substantially from a heat insulating or thermally non-conductive material, and the flange also preferably includes a shoulder portion adapted to cooperate with the means for retaining the probe.

In combination with the infrared radiation detecting device, the probe is adapted to be ejected from the device by at least one push rod in the device. A plurality of detents project radially inwardly to accept the probe and are adapted to engage the flange of the probe.

Other aspects and advantages of the invention will become apparent from the following detailed description and the accompanying drawings illustrating by way of example the features of the invention.

BRIEF DESCRIPTION OF THE DRAWINGS

FIG. 4 is a cross-sectional view of the insertion probe of FIG. 1 in combination with an infrared radiation detecting device; and FIG. 5 is cross-sectional view of the probe of FIG. 3 in combination with an alternate infrared radiation detecting device.

DETAILED DESCRIPTION OF THE INVENTION

Figure 1:
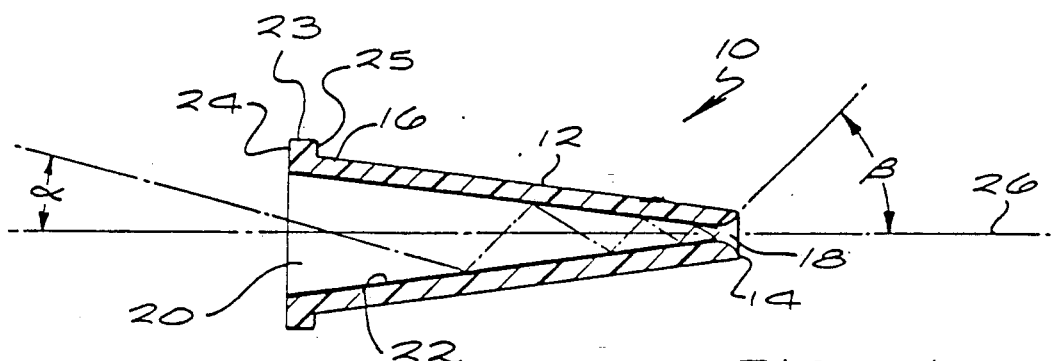
FIG. 1 is a cross-sectional view of one embodiment of the disposable insertion probe.

As is shown in the drawings for purposes of illustration, the invention is embodied in a probe for use in combination with an infrared radiation detecting device. The probe is disposable, and may be used in combination with the infrared detecting device as a medical infrared thermometer for taking temperatures of patients by way of the auditory canal, or other body cavities. The probe is open at both ends and includes an inner reflective surface to maximize its performance as a negative cone channel objective lens in collimating infrared radiation from a wide acceptance angle.

In accordance with the invention, there is provided a probe for use in combination with an infrared radiation detecting device, having means for retaining said probe, and means for focusing infrared radiation transmitted through said probe to an infrared sensor, said probe comprising a generally frusto-conical body portion having a narrow forward end and a wide rearward end; said body portion having an inner reflective surface; and flange means projecting radially outward from said body portion for abutting a portion of said device.

In addition, the invention provides for the combination of an infrared thermometer having means for focusing infra-red radiation on an infrared radiation sensor, and a negative cone-channel collimating probe, said infrared detecting device having means for releasably retaining said probe, said probe comprising: a generally frusto-conical body portion having a narrow forward end and a wide rearward end; said body portion having an inner reflective surface; and flange means projecting radially outward from said body portion for abutting a portion of said device; whereby said probe functions as an objective lens of said infrared radiation detecting device.

As is shown in the drawings, a preferred disposable infrared thermometer insertion probe 10 includes a body portion 12, a narrowed forward end 14, and a widened rearward end 16. The probe thus has the general shape of a truncated hollow cone. The frusto-conical hollow body is open at the forward and rearward ends 18 and 20 to allow for maximum transmission of infrared radiation through the probe. The body portion is also preferably composed substantially of a closed cell plastic foam, such as polystyrene, which serves as insulation to prevent the probe from absorbing or thermally conducting heat from any source. In addition, the probe has an inner reflective surface 22, whose primary purpose is reflecting infrared radiation entering at the forward opening 18 through the probe to exit at the rearward end, without substantial diminution in the amount of infrared radiation collected. Another major advantage of the high reflectance of the inner surface is the reduction of infrared radiation being absorbed by the probe, to prevent the probe from acting as a radiating body itself, which would tend to introduce error in the temperature readings of the detector. In the preferred embodiment, the inner reflective surface of the body portion is made of a Mylar film, a product of Du Pont de Nemours, E. I. & Co., which is essentially a polyester film having a highly reflective aluminized surface which will give a reflective of about 99% in the probe. Alternatively, the inner surface of the body portion itself may be provided with a metallized reflective surface, such as by vapor deposition of a reflective metal upon the inner surface of the body of the probe. A further alternative is to provide a dielectric coating over a metalized inner surface of the probe body. Such a dielectric coating may be, for example, $MgS_2$, which will prevent oxidation of an aluminum surface and provide abrasion resistance. Although aluminum is the metal of choice for metalization of the inner surface, other coatings which would provide an inexpensive high reflection surface may also be appropriate.

With reference to FIG. 1, a preferred disposable insertion probe also includes a flange 23 projecting radially outward from the rearward end of the probe, to provide an abutment surface 24 on the flange for abutting a surface of the housing or retaining means of the infrared thermometer. Since the probe serves as an objective lens, and the focal length of the probe with respect to the internal optics of the infrared thermometer is critical, the abutment edge 24 of the flange allows for accurate positioning of the probe with respect to the infrared thermometer. A shoulder portion 25 on the forward edge of the flange 23 offers a surface for engagement by retaining means on the infrared thermometer, as will be further described hereinafter.

About the center line 26 of the probe at the forward end 14, the acceptance half angle $\beta$ represents the widest angle at which infrared radiation will be accepted by the probe and transmitted to exit through the rearward end. The exit half angle $\alpha$ represents the angle about the center line at which the infrared radiation entering at the maximum acceptance half angle $\beta$ will exit the rearward end of the probe. In terms of discussing the probe as an objective lens, the numerical aperture of the probe is the sine of acceptance half angle $\beta$. A design goal for the dimensions and optics of the probe is to provide as large a numerical aperture as possible for the acceptance half angle $\beta$ and as small a numerical aperture as possible for the exit angle $\alpha$. The probe therefore performs as a negative or diverging cone channel object lens. The small numerical aperture at the rearward end of the probe means that the energy transmitted through the probe is largely but not completely collimated. It is therefore necessary to provide further condensation of the optical field with one or more auxiliary lenses. The further condensation of the infrared radiation is accomplished with a focusing lens and a positive cone channel condensor detector field lens, which will be described further.

Because of the minute temperature differences between the cooler temperatures of the human body and the ambient temperatures of the infrared thermometer, it is important to receive as much optical signal as possible from the body cavity. At the same time, it is necessary to minimize the size of the probe that contains the objective lenses, so that the probe can penetrate sufficiently into the body cavity, such as an ear canal. A typical inner diameter at the forward end of the insertion probe may be 0.5 cm or smaller, so that the probe of the present invention therefore utilizes the focusing characteristics of a cone channel collimating lens to maximize the numerical aperture of the object end of the objective lens. The energy collecting ability of the objective lens is proportional to the square of the numerical aperture of the lens. The optical gain of the probe as an objective lens is proportional to $R_1{}^2 \sin^2 \beta$, where $R_1$ is the aperature radius at the forward or objective end of the probe. The collimating power or the focusing power of the lens is $R_2/R_1$ where $R_2$ is the radius of the aperture at the image or rearward end of the probe. The theoretical maximum of the acceptance half angle beta is 90°, and although it is desirable to collimate infrared radiation received at the object end of the probe into a beam as nearly parallel to the optical axis or center line as possible, from a practical standpoint the exiting beam will have an appreciable diverging angle $\alpha$, where $\alpha = R_1/R_2 \times \beta$. For example, where the object end aperture radius is 0.1 inches and the exit or image aperture radius is 0.25 inches, given a probe length of approximately three inches, the exit angle $\alpha$ would be approximately 35°. Narrowing the object aperture radius to 0.05 inches would produce an exit angle $\alpha$ of approximately 17 degrees. Therefore, the diverging beam from the probe requires a further positive, focusing lens to further collimate and focus the infrared radiation to the infrared sensor.

Since the inner surface of the probe is an excellent reflector, the absorptance and emissivity of the inner surface are minimal so that the probe would not be expected to radiate error signals to the detector, even if the inner surface of the probe is at a temperature different from that of the detector. Thus, the inner surface of the probe need not provide good insulation, but the outer surface of the probe should not absorb or conduct thermal energy from the walls of the cavity into which it is inserted, which would upset the cavity's thermal balance, which is to be measured. Therefore, the outside surface of the probe should consist substantially of a material which is a good insulator, such as a polystyrene closed cell plastic foam, which would possess a very low thermal capacity, and very low thermal conductivity.

Figure 2:
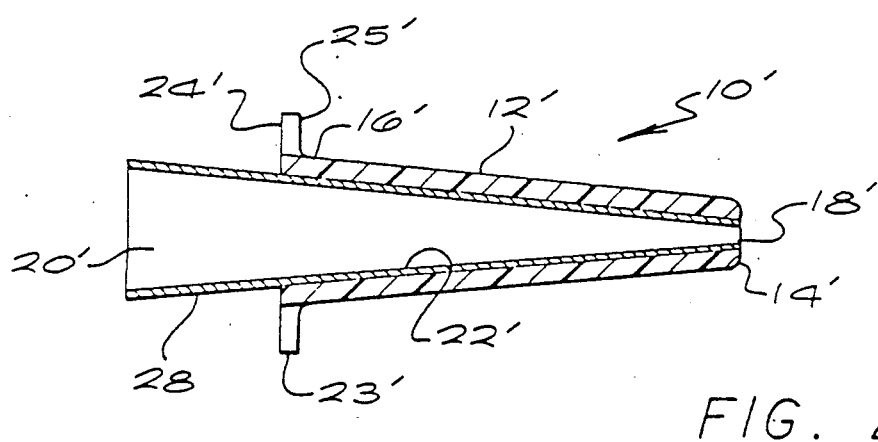
FIG. 2 is a cross-sectional view of a second embodiment of a disposable insertion probe.

With reference to FIG. 2 a second embodiment of the insertion probe includes a frusto-conical extension 28 of the inner surface 22' beyond the rearward end 16' and the flange 23'. It is important that the optical reflecting surface of the probe cone extend very close to the internal optics of the infrared thermometer, particularly as some amount of the infrared radiation will be diverging from the rearward end of the probe, which would result in the loss of some of this radiation and possibly some absorption of the radiation by portions of the housing of the infrared thermometer.

Figure 3:
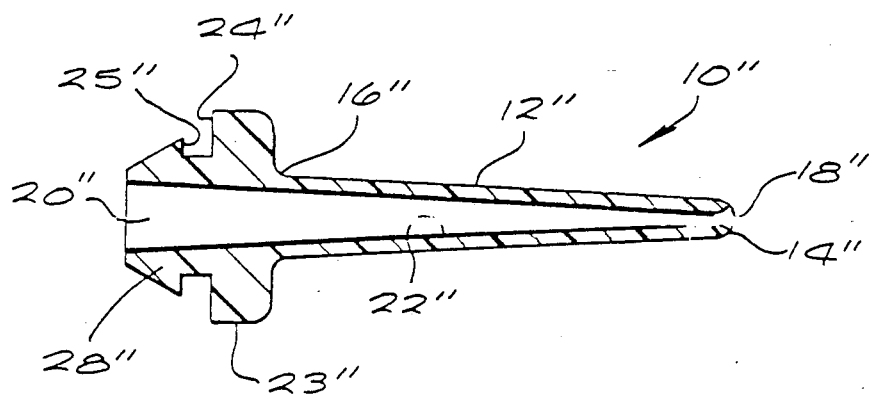
FIG. 3 is a cross-sectional view of a third embodiment of the disposable insertion probe.

With references to FIGS. 3 and 5, a third embodiment of the insertion probe also includes an extension 20" of the internal reflecting surface rearward of the rearward end and flange. The extension portion can be seen in FIG. 5 to extend very close to the focusing lens of the internal optics of the infrared thermometer. Further with reference to FIG. 4, it can be seen how the probe 10 is secured to and released from the housing of the infrared thermometer. The jaws or detents 30a and 30b move radially inwardly and outwardly to grasp the shoulder portions 25, 25', 25"(FIGS. 1-3). Abutment surfaces 24, 24' and 24" abuts against a portion of the housing of the infrared thermometer, for accurate positioning of the insertion probe. The infrared thermometer includes a layer of insulation to keep the optics and sensor at a relatively stable temperature. Referring again to FIG. 4, also provided is a high mass heat sink 34, preferably of aluminum, contained within the housing 36 of the infrared thermometer. A shutter mechanism 37 is provided between the insertion probe and the focusing lens 38, located at the wide end of a positive condensor cone channel 39. Located at the image end of the condensor cone channel is a detector sensor 40, which may include a band-pass interference filter to block all wavelengths shorter than 7 microns and longer than 20 microns, allowing wavelengths between 7 microns and 20 microns to pass to the sensor. In the preferred embodiment, as is shown in FIG. 4, one or more push rods 42a, 42b are provided to allow the operator of the infrared thermometer to eject the insertion probe. O-rings 43 seal the passageways for the push rods from the entrance of extraneous heat which may cause errors in the fine readings of the infrared sensor. A spring 44 may also be provided for spring actuation of the ejection mechanism, which may be assisted by pressure on the push button 45. The biasing of the push rod by the spring 44 in a forward direction is also useful in the detection of an error condition in which the insertion probe may not be fully seated. For detection of such an error condition, there is provided a flange 46 on a push rod positioned to contact a switch 48 having connections 50 and 52 to the circuitry of the signal processing portion of the infrared thermometer, for generating signal indicating an error condition when the push rod flange is not in contact with the switch 48.

The reflective inner surface of the insertion probe could also be composed of a dielectric film which has a thickness equal to an odd number of quarter peak infrared wavelengths utilized by the detector is $\lambda$ micrometers, then dielectric walls having thicknesses of one-quarter $\lambda$, three-quarter $\lambda$, five-quarter $\lambda$, and the like would cause total internal reflection and therefore contain the infrared radiation. Also, a tapered light pipe could also serve to provide the inner reflective surface on the insertion probe. The light pipe would have a central cone channel core of the same dimensions as the objective lens described above and would be subject to the same general mathematical principles. The materials used to construct the cone channel would be highly transmissive in the part of the electro-magnetic spectrum used by the detector, 7 microns to 20 microns, such as ZnSe, $GEBaF_2$, KRS-6, KRS-5, the like. The outer surface of the cone channel light pipe material would be clad with a material possessing a higher index of refraction than the cone material, thereby effecting total internal reflection of the infrared waves at the interface of the materials with differing indices of refraction. Although the insertion probe cone channel would not be hollow, in this configuration, the transmission of infrared radiation would not be occluded by films on the exterior surface of the insertion probe.

In order to optimize the performance characteristics of the insertion probe as an objective lens, it would be desirable to make the cone channel as long as possible, and to make the object end of the probe with as small an outside diameter as possible while making the image end of the cone channel inside diameter as large as possible. It would also be desirable to maximize the collimation powers of the insertion probe as much as possible by making the ratio of the rearward or image end diameter to the diameter of the forward or objective end of the probe as large as possible.

In the foregoing description, it has been demonstrated that the disposable infrared thermometer insertion probe of the present invention provides a negative cone channel objective lens for an infrared thermometer, to insure the accuracy of infrared temperature readings, and sterile conditions for making such readings in a clinical situation. The cone channel insertion probe may be quickly and easily placed onto the infrared thermometer, and ejected for sanitary disposal Although the insertion probe has been described for use with an infrared thermometer, it is clear that the insertion probe may also be used with other infrared detecting devices, and even other devices for measurement of other types of electromagnetic radiation, such as visible light or ultraviolet light.

Although a preferred embodiment of the invention has been described and illustrated, it is clear that it is susceptible to numerous modifications and embodiments within the ability of those skilled in the art, and without the exercise of the inventive faculty. Thus, it should be understood that various changes in form, detail and application of the present invention may be made without departing from the spirit and scope of this invention.

I claim:

1. In combination with an infrared radiation detecting device, an apparatus for focusing infra-red radiation on an infrared radiation sensor mounted in the detecting device, said apparatus comprising:
   a) a probe comprising:
      1) a generally tubular, frusto-conical, thermally insulating body portion having a narrow forward end and a wide rearward end, said body portion having an inner reflective surface which is continually frusto-conical in shape from the forward end to the rearward end; and
      2) flange means projecting radially outward from said body portion for abutting a portion of the detecting device, said flange means including a shoulder for abutting the detecting device and also including a detent;
   whereby said probe functions as an objective lens of said infrared radiation detecting device;
   b) releasable retaining means for retaining the probe in a predetermined position on the detecting device and for releasing the probe from said predetermined position so that it may be replaced with another probe, said retaining means including locking means for engaging the detent of the flange for locking the probe in the predetermined position on the detector device;
   c) a focusing lens disposed in the detector device at the rearward end of the probe; and
   d) a positive cone channel condensor lens coupled between the focusing lens and the energy detecting device.

2. In combination with an infrared radiation detecting device, an apparatus for focusing infra-red radiation on an infrared radiation sensor mounted in the detecting device, said apparatus comprising:
   a) a probe comprising:
      1) a generally tubular, frusto-conical, thermally insulating body portion having a narrow forward end and a wide rearward end, said body portion having an inner reflective surface which is continually frusto-conical in shape from the forward end to the rearward end; and
      2) flange means projecting radially outward from said body portion for abutting a portion of the detecting device said flange means comprising a shoulder for abutting the detecting device;
   whereby said probe functions as an objective lens of said infrared radiation detecting device;
   b) releasable retaining means for retaining the probe in a predetermined position on the detecting device and for releasing the probe from said predetermined position so that it may be replaced with another probe, the releasable retaining means comprising a jaw for engaging the shoulder of the flange means to lock the probe in the predetermined position;
   c) a focusing lens disposed in the detector device at the rearward end of the probe; and
   d) a positive cone channel condenser lens coupled between the focusing lens and the energy detecting device.

3. In combination with an infrared thermometer, an apparatus for focusing infra-red radiation on an infrared radiation sensor mounted in the thermometer, said apparatus comprising:
   a) a probe comprising:
      1) a generally tubular, frusto-conical, thermally insulating body portion having a narrow forward end and a wide rearward end, said body portion having an inner reflective surface which is continually frusto-conical in shape from the forward end to the rearward end; and
      2) flange means projecting radially outward from said body portion for abutting a portion of said thermometer, said flange means including a shoulder for abutting the thermometer and also including a detent;
   whereby said probe functions as an objective lens of said infrared thermometer;
   b) releasable retaining means for retaining the probe in a predetermined position on the thermometer and for releasing the probe from said predetermined position so that it may be replaced with another probe, said retaining means including locking means for engaging the detent of the flange means for locking the probe in the predetermined position on the thermometer;
   c) a focusing lens disposed in the thermometer at the rearward end of the probe; and
   d) a positive cone channel condenser lens coupled between the focusing lens and the sensor.

4. In combination with an infrared thermometer, an apparatus for focusing infra-red radiation on an infrared radiation sensor mounted in the thermometer, said apparatus comprising:
   a) a probe comprising:
      1) a generally tubular, frusto-conical, thermally insulating body portion having a narrow forward end and a wide rearward end, said body portion having an inner reflective surface which is continually frusto-conical in shape from the forward end to the rearward end; and
      2) flange means projecting radially outward from said body portion for abutting a portion of said thermometer, said flange means comprising a shoulder for abutting the thermometer;

whereby said probe functions as an objective lens of said infrared thermometer;

b) releasable retaining means for retaining the probe in a predetermined position on the thermometer and for releasing the probe from said predetermined position so that it may be replaced with another probe, the releasable retaining means comprising a jaw for engaging the shoulder of the flange means to lock the probe in the predetermined position;

c) a focusing lens disposed in the thermometer at the rearward end of the probe; and d) a positive cone channel condensor lens coupled between the focusing lens and the sensor.

* * * * *

UNITED STATES PATENT AND TRADEMARK OFFICE
CERTIFICATE OF CORRECTION

PATENT NO. : 5,046,482
DATED      : September 10, 1991
INVENTOR(S): Charles E. Everest It is certified that error appears in the above-identified patent and that said Letters Patent is hereby corrected as shown below:

Column 6:

Line 40, insert after the word "quarter"

-- wavelengths of the infrared lengths. Therefore, if the --

Signed and Sealed this

Twenty-seventh Day of April, 1993

Attest:

MICHAEL K. KIRK

Attesting Officer

Acting Commissioner of Patents and Trademarks